(12) United States Patent
Douglass et al.

(10) Patent No.: US 12,016,370 B2
(45) Date of Patent: Jun. 25, 2024

(54) SOLVENTLESS METHOD OF PRODUCING COATED BOTANICAL SUBSTRATES

(71) Applicant: Scientific Holdings, LLC, Monrovia, CA (US)

(72) Inventors: Bradley J. Douglass, Monrovia, CA (US); Jeffrey Charles Raber, Monrovia, CA (US)

(73) Assignee: Scientific Holdings, LLC, Commerce, CA (US)

( * ) Notice: Subject to any disclaimer, the term of this patent is extended or adjusted under 35 U.S.C. 154(b) by 0 days.

(21) Appl. No.: 17/898,464

(22) Filed: Aug. 29, 2022

(65) Prior Publication Data

US 2024/0065309 A1    Feb. 29, 2024

(51) Int. Cl.
| | |
|---|---|
| A24B 15/16 | (2020.01) |
| A24B 15/18 | (2006.01) |
| A24B 15/28 | (2006.01) |
| A24B 15/30 | (2006.01) |
| A61K 31/05 | (2006.01) |
| B01F 29/15 | (2022.01) |
| B01F 101/22 | (2022.01) |

(52) U.S. Cl.
CPC ............ *A24B 15/186* (2013.01); *A24B 15/16* (2013.01); *A24B 15/285* (2013.01); *A24B 15/303* (2013.01); *A61K 31/05* (2013.01); *B01F 29/15* (2022.01); *B01F 2101/22* (2022.01)

(58) Field of Classification Search
None
See application file for complete search history.

(56) References Cited

U.S. PATENT DOCUMENTS

| | | | |
|---|---|---|---|
| 10,434,084 B2* | 10/2019 | Raber | A61K 9/1676 |
| 2011/0275518 A1* | 11/2011 | Marques | A01C 1/02 |
| | | | 423/604 |
| 2019/0015383 A1* | 1/2019 | Woelfel | A61K 31/05 |

* cited by examiner

*Primary Examiner* — Dennis R Cordray
(74) *Attorney, Agent, or Firm* — Foundation Law Group LLP; JD Harriman

(57) ABSTRACT

The disclosure provides a solventless method of producing coated botanical substrates by (i) uniformly coating a known exact amount of an active ingredient on the botanical substrates until the ingredient is substantially adsorbed to the surface of the botanical substrate to produce a homogeneous primary coating of the ingredient on the botanical substrates, and optionally (ii) substantially incorporating a flavoring agent with the surface of the plurality of botanical substrates coated with the ingredient.

22 Claims, 1 Drawing Sheet

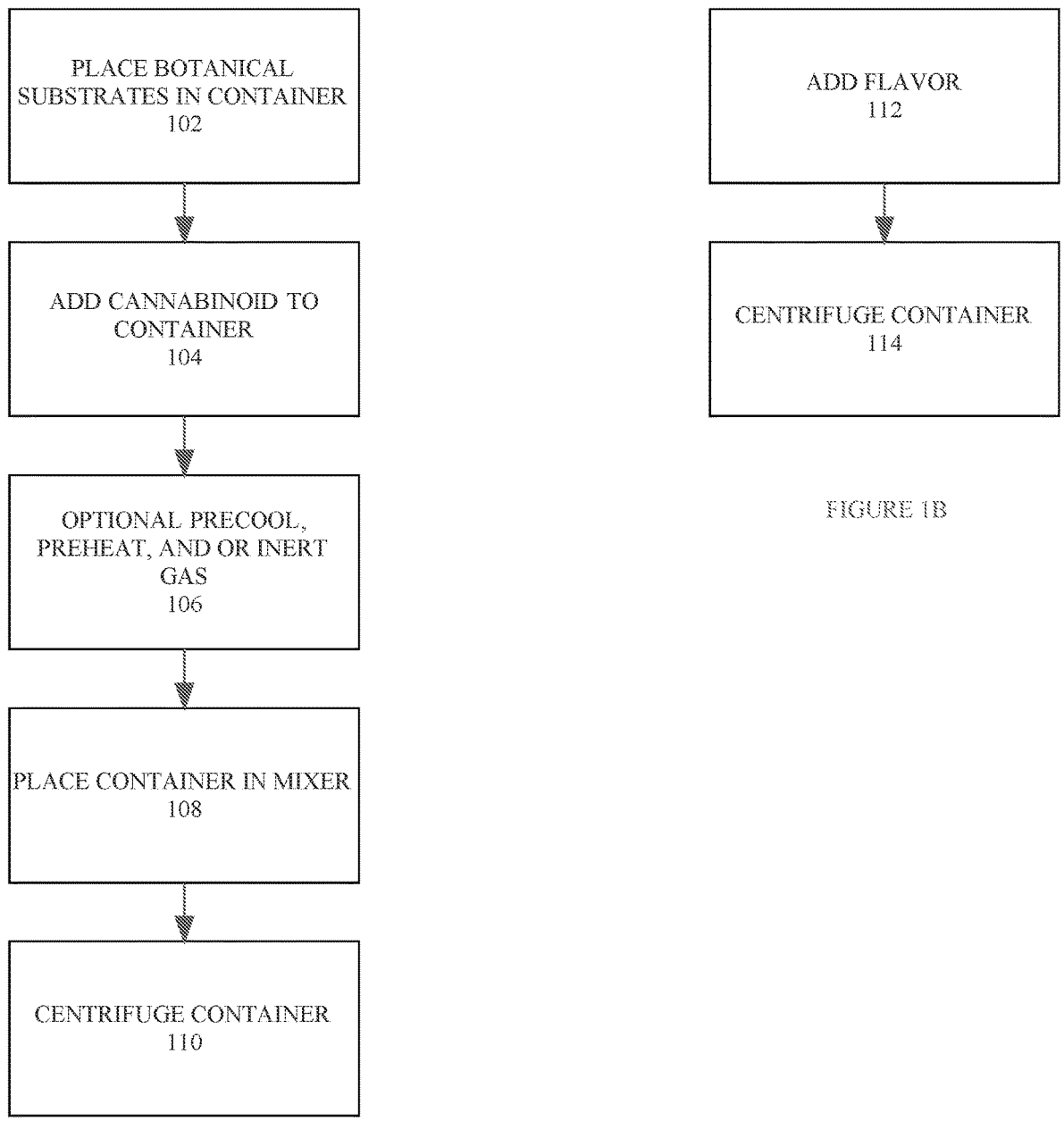

SOLVENTLESS METHOD OF PRODUCING COATED BOTANICAL SUBSTRATES

BACKGROUND

Technical Field

Embodiments of this disclosure generally relate to smokable products comprising as additives one or more ingredients that function as harm reduction and/or experience-enhancing agents and to a solventless method of producing coated botanical substrates with cannabinoids.

Background

Herbal smoking products are popular around the world. A veritable litany of herbs, blends, infusions, and flavors are available, purchased, and sold for this purpose. While tobacco (*Nicotiana* spp.) is perhaps the most popular botanical substrate or herbal base used for smoking, cannabis (*Cannabis* spp), marshmallow (*Althaea* spp.), and damiana (*Turnera* spp.) are also popular botanical substrates. Importantly, inhalation routes of administration of herbal bases may offer exceptional utility in modulating or improving physiological activity within humans. An excellent example of positive physiological responses being provided through smoking an herbal product can be seen in the plethora of *cannabis* products on the market today.

Herbal bases comprise a mixture of more than one botanical substrate. One purpose for using a botanical substrate or herbal base in herbal smoking products is to incorporate specific functional characteristics into the product or to elicit specific physiological effects in the user. Some functions include but are not limited to eliciting a sensory perception, altering or improving the overall smoking experience, or any combination thereof. Common methods of incorporation of these various ingredients include spraying and soaking liquid substances onto the botanical substrate or herbal base component(s).

Soaking methods require the use of excess ingredients in the manufacture of these products. This generates both physical and economic waste. A further limitation of soaking approaches is the typical requirement for completely saturating the botanical substrate with the ingredient. This approach does not permit the flexibility to fine-tune the amount of the liquid substance. In addition, it can make it difficult to achieve uniform distribution of the liquid substance on the substrate. This greatly hampers the development, exploration, and utility of herbal formulations meant for inhalation due to limited dosage control, or inconsistent concentration of ingredients. In many cases, this limited dosage control can prove deleterious or lead to undesirable characteristics (e.g., off-taste).

Spraying or spray-drying ingredients onto a botanical substrate presents challenges in creating a uniform and homogeneous distribution of ingredients across the herbal substrate. Additionally, spraying requires liquid formulations. The creation of a flowable fluid is often achieved through the addition of solvents or solvent-like substances which further limit ingredient dosing flexibility and additionally add to the costs of production of the product. Water is generally avoided because introducing moisture to botanical substrates is: 1) difficult to then remove, 2) encourages microbial growth and/or 3) negatively impacts the texture and bulk structure of the botanical materials. The introduced non-uniformity then presents challenges in the creation of products that would function consistently. For example, uneven distribution of a flavoring may lead to an undesired and deleterious inhalation experience due to off-flavors or an uneven burn.

There remains a need for an improved method of incorporating, combining, adhering, admixing, and introducing ingredients of interest to botanical substrates and herbal bases.

SUMMARY

Accordingly, a solvent-less method of producing coated botanical substrates and herbal bases is provided. The method includes placing a plurality of botanical substrates in a container. At least one ingredient of interest is added to the container comprising the plurality of botanical substrates or herbal bases (hereto forward abbreviated as simply "botanical substrates"). The container comprising the plurality of botanical substrates and the at least one ingredient of interest is placed in a mixing device that applies centripetal and shear forces to the constituents as the primary driver of mixing (hereto forward abbreviated as simply "mixer") and mixed until the ingredient or ingredients of interest are substantially adsorbed to the surface of the plurality of botanical substrates to produce a primary coating of the ingredient of interest on the plurality of botanical substrates. A flavoring agent may optionally be added to the container including the botanical substrates coated with the at least one ingredient of interest and centrifuged in the mixer until the flavoring agent is substantially incorporated onto the surface of the plurality of botanical substrates coated with the at least one ingredient of interest. The method optionally includes pre-cooling the container, pre-heating the container before use, and evacuating the container with an inert gas to produce an oxygen-reduced environment (relative to atmospheric air).

According to one embodiment, the method includes activating the mixer at 2000 RPM for approximately 90 seconds to produce the primary coating of the ingredient(s) of interest on the botanical substrates.

According to one embodiment, the method includes activating the mixer at 2000 RPM for about 20 seconds to substantially adsorb the flavoring agent onto the surface of the plurality of botanical substrates coated with the ingredient(s) of interest.

According to one embodiment, the botanical substrate has an average particle size ranging from 0.1 mm to 20 mm.

According to one embodiment, the botanical substrate includes *Althaea officinalis* L (marshmallow leaf), *Amaranthus dubius, Arctostaphylos* uva-ursi (bearberry), *Argemone mexicana, Arnica, Artemisia vulgaris* (mugwort), Asteraceae (chamomile), *Brassica oleracea* (cabbage), *Calea zacatechichi, Cannabis sativa* (*cannabis*/marijuana or 80 hemp), *Canavalia maritima* (baybean), *Cecropia obtusifolia, Cestrum nocturnum, Cynoglossum virginianum* (wild comfrey), *Cytisus scoparius, Entada rheedii, Eschscholzia californica* (California poppy), *Fittonia albivenis, Humulus japonicus* (Japanese hops), *Lavandula* (lavender), *Lactuca virosa* (lettuce opium), Lamiaceae (mint), *Salvia* (sage), *Scutellaria* (skullcap), *Leonotis leonurus* (lion's tail), *Leonurus cardiaca* (motherwort), 85 *Leonurus sibiricus* (honeyweed), *Lobelia cardinalis, Lobelia inflata* (Indian tobacco), *Lobelia siphilitica, Nepeta cataria* (catnip), *Nicotiana, Nymphaea alba* (white lily), *Nymphaea caerulea* (blue lily), *Papaver somniferum* (opium poppy), *Origanum majorana* (marjoram), *Origanum vulgare* (oregano), *Passiflora incarnata* (passionflower), *Pedicularis densiflora* (Indian warrior), *Pedicularis groenlandica* (elephant's head),

*Rubus idaeus* (red raspberry), 90 *Rubus occidentalis, Salvia divinorum, Salvia dorrii* (tobacco sage), *Scutellaria galericulata, Scutellaria lateriflora, Scutellaria nana, Sida acuta* and/or *Sida rhombifolia* (wireweed), *Silene capensis, Syzygium aromaticum* (clove), *Tagetes lucida* (Mexican tarragon), *Tarchonanthus camphoratus, Turnera diffusa* (damiana), *Tussilago farfara* (coltsfoot), *Verbascum* (mullein), *Zornia latifolia* (maconha brava), or mixtures thereof.

According to one embodiment, the cannabinoid is obtained as an extract or pure form including liquids, solids, slurries, botanical substrate pastes, and wetted solids.

According to one embodiment, the cannabinoid comprises at least one of Δ-9-tetrahydrocannabinol (D9-THC) cannabidiol (CBD), cannabigerolic acid (CBGA), cannabigerol (CBG), cannabigerol monomethylether (CBGM), cannabigerovarin (CBGV), cannabichromene (CBC), cannabichromevarin (CBCV), cannabidiol monomethylether (CBDM), cannabidiol-C4 (CBD-C4), cannabidivarin (CBDV), cannabidiorcol (CBD-C1), Δ-9-tetrahydrocannabinolic acid A (THCA-A), Δ-9-tetrahydrocannabinolic acid B (THCA-B), Δ-9-tetrahydrocannabinolic acid-C4 (THCA-C4), Δ-9-tetrahydrocannabinol-C4, Δ-9-tetrahydrocannabivarin (THCV), Δ-9-tetrahydrocannabiorcol (THC-C1), Δ-7-cis-iso tetrahydrocannabivarin, Δ-8-tetrahydrocannabinol (D8-THC), cannabicyclol (CBL), cannabicyclovarin (CBLV), cannabielsoin (CBE), cannabinol (CBN), cannabinol methylether (CBNM), cannabinol-C4 (CBN-C4), cannabivarin (CBV), cannabinol-C2 (CBN-C2), cannabiorcol (CBN-C1), cannabinodiol (CBND), cannabinodivarin (CBVD), cannabitriol (CBT), 10-ethoxy-9 hydroxy-Δ-6a-tetrahydrocannabinol, 8,9-dihydroxy-Δ-6a-110 tetrahydrocannabinol, cannabitriolvarin (CBTV), ethoxy-cannabitriolvarin (CBTVE), dehydrocannabifuran (DCBF), cannabifuran (CBF), cannabichromanon (CBCN), cannabicitran (CBT), 10-oxo-Δ-6a-tetrahydrocannabinol (OTHC), Δ-9-cis-tetrahydrocannabinol (cis-THC), 3,4,5,6-tetrahydro-7-hydroxy-α-α-2-trimethyl-9-n-propyl-2,6-methano-2H-1-benzoxocin-5-methanol (OH-iso-HHCV), cannabiripsol (CBR), 115 trihydroxy-Δ-9-tetrahydrocannabinol (triOH-THC), cannabinol propyl variant (CBNV), cannabidiolic acid (CBDA), cannabitriol (CBO), and tetrahydrocannabivarinic acid (THCVA) and all isomers and analogues of the above.

According to one embodiment, the flavoring agent is a blend of naturally-occurring constituents, including terpenes, which mimics the aroma and taste of a *cannabis* cultivar.

According to one embodiment, the mixer is a dual asymmetrical centrifuge (DAC) mixer.

According to one embodiment, the plurality of coated botanical substrates has a coated particle mass (grams). The plurality of botanical substrates has a mass that ranges 125 from 55% to 99.3% of the coated particle mass, the ingredient(s) of interest in the plurality of coated botanical substrates has a mass that ranges from 0.5% to 45% the coated particle mass, and the flavoring agent(s) in the plurality of coated botanical substrates has a mass that ranges from 0.2% to 10% of the coated particle mass.

According to one embodiment, the pre-cooling of the container is performed 130 at about −5 degrees C., −10 degrees C., −15 degrees C., −20 degrees C., −25 degrees C., −30 degrees C., −40 degrees C., or −78 degrees C.

According to one embodiment, the method further comprises coating the botanical substrate with multiple layers of additional ingredients that further stabilize the augmented herbal smoking product, such as a coated herbal substrate that mimics *cannabis*.

According to one embodiment, the botanical substrate is coated with nicotine or nicotine salts, either derived from tobacco, a microbial platform, or produced synthetically, with or without additional active ingredients or flavoring to produce a tobacco tapering product.

According to one embodiment, the plurality of coated botanical substrates has a coated particle mass (grams). The plurality of botanical substrates has a mass that ranges from 95% to 99% the coated particle mass, the nicotine in the plurality of coated botanical substrates has a mass that ranges from 0.1% to 1.3% the coated particle mass, and the flavoring agent in the plurality of coated botanical substrates has a mass that ranges from 1% to 5% the coated particle mass.

Economic advantages can be gained whereby the method of the system is solventless or utilizes non-solvent like substances to improve manufacturing efforts in the creation of such products. Further economic gains, ingredient use efficiencies, waste stream capture, and process fine-tunability can be gained through the method of the system whereby an appropriate amount of desired ingredients are utilized, without the need for excess ingredients to achieve the desired result. New product opportunities, product possibilities, and new product categories of herbal blends can thereby be created by the method of the system which offers economic and functional utility without the current limitations in the field, i.e. product inconsistency, microbial/solvent contamination, and ingredient-state limitations.

BRIEF DESCRIPTION OF THE DRAWINGS

The embodiments herein will be better understood from the following detailed description with reference to the drawings, in which:

FIGS. 1A and 1B are flow diagrams that illustrate a solventless method of producing coated botanical substrates according to some embodiments herein.

DETAILED DESCRIPTION OF PREFERRED EMBODIMENTS

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a step" includes single or plural steps and is considered equivalent to the phrase "comprising at least one step." The term "or" refers to a single element of stated alternative elements or a combination of two or more elements, unless the context clearly indicates otherwise. As used herein, "comprises" means "includes." Thus, "comprising terpenes", means "including terpenes", without excluding additional elements. All references, including journal articles, patents, and patent publications cited herein are incorporated by reference in their entirety as if each individual journal article, patent, or patent publication, was specifically and individually indicated to be incorporated by reference in its entirety for all purposes.

FIGS. 1A and 1B are flow diagrams that illustrate a solventless method of producing coated botanical substrates according to some embodiments herein. In step 102, the method 100 includes placing a plurality of botanical substrates in a container. In step 104, 175 the method includes adding a cannabinoid into the container with the plurality of botanical substrates. In optional step 116, the system comprises one or more of: (a) pre-cooling the container, (b), pre-heating the container before use and (c) evacuating the container with an inert gas to produce an oxygen-free environment. In step 108, the method includes placing the container comprising the plurality of botanical substrates and the cannabinoid in a mixer. In step 110, the method includes centrifuging the container in the mixer until the cannabinoid is substantially adsorbed to the surface of the plurality of botanical substrates to produce a homogeneous primary coating of the cannabinoid on the plurality of botanical substrates. In step 112, the method includes adding a flavoring agent into the container comprising the plurality of botanical substrates coated with the cannabinoid. In step 114, the method includes 185 centrifuging the container in the mixer until the flavoring agent is substantially incorporated with the surface of the plurality of botanical substrates coated with the cannabinoid, resulting in the coated botanical substrates.

Cannabinoids that are only solids, or only liquids, may also be used, both by themselves and in various combinations with one another. A particularly preferred embodiment of this method involves the use of active ingredients in their solid form. Solventless introduction of these solid ingredients in a uniformly distributed fashion can effectively be achieved with a variety of botanical substrates. A variety of active ingredients, such as nicotine salts, cannabinoids, and cannabinoid acids are solids at room temperature and are amenable to the process described herein.

Mixing of the cannabinoid with the botanical substrates may use a similar approach, for example, as described by U.S. Pat. No. 10,434,084 of Raber, Jeffrey; Douglass, Bradley; and Doane, Braden which is incorporated herein by reference in its entirety. The use of dual asymmetric centrifugation facilitates the introduction of specific and quantifiable exact known amounts of cannabinoids onto a variety of botanical substrates. Dual asymmetrical centrifuge (DAC) differs from conventional centrifugation by an additional rotation of the sample around its vertical axis. While the conventional centrifugation constantly pushes the sample material outwards, this additional rotation constantly forces the sample material towards the center of the centrifuge. This combination of two contra-rotating movements results in shear forces and thus, in efficient homogenization (Massing et al (2008) *Dual asymmetric centrifugation (DAC)-a new technique for liposome preparation*. J. Control Release. 125:16-24). Non-limiting information about one model of DAC reveals that, the dual asymmetric DAC 150 FV-K works by spinning a high speed-mixing arm at speeds up to 3700 rpm in one direction while the basket rotates in the opposite direction, thus, the name, dual asymmetric centrifuge. This combination of forces in different planes enables fast mixing, and yet the precision construction of each machine gives it a balance that allows quiet operation (Synergy Devices (Oct. 11, 2006). Non-limiting information on another model of DAC reveal that the mixing procedure is based on the double rotation of the mixing cup (hence the designation dual asymmetric centrifuge). This combination of centrifugal forces acting on different levels enables very rapid mixing of the entire container. The precision construction of the units gives the opposing forces an equilibrium with near zero vibration and low-noise operation.

The method of the system can be used to create products that mimic botanical substrates, such as imitation *cannabis*, for a variety of pharmaceutical, medicinal, and recreational uses. Both cannabinoids and terpenes can be introduced to different botanical substrates and plant matrices to create products whose analytical chemical profile closely resembles that of a *cannabis* plant. Terpenes that may be used well with cannabinoids may be those as described by U.S. Pat. No. 10,774,288 by Elzinga, Sytze and Raber, Jeffrey which is incorporated herein by reference in its entirety. Other active ingredients, like nicotine, can also be used, with and without terpenes, to create novel tobacco tapering products. These products are created using various amounts of nicotine while keeping all the remaining smell and taste attributes the same. This has the benefit of providing a similar smoking experience without using tobacco or tobacco-derived ingredients while exerting fine-control over the concentration of active constituents, such as nicotine. This enables users to utilize a step-down system (i.e.) a "tapering" approach that deploys decreased nicotine amounts over time to help reduce any potential chemical withdrawal symptoms while aiming to cease the use of tobacco. Similarly, caffeine in tea or coffee could be slowly reduced over time while the experience doesn't change otherwise. Typically, plants that are grown to lower active ingredient content also result in other plant metabolites being present in lower concentrations. Likewise, when botanical substrates are treated to remove or reduce one (e.g., decaffeinated coffee) or multiple active constituents, others are often diminished unintentionally. Fewer flavor molecules being produced means a drastically different taste and overall smoking experience. The mixing method of the system allows for olfactory, sensory, perceptual, and other functional ingredients to be held at a fixed concentration while as few as only one active ingredient, or more, could be decreased, increased, eliminated, or otherwise held constant relative to the rest of the formulation. Complete removal of only one active ingredient could provide an effective placebo that would be useful in both clinical studies and cessation programs.

The method of the system allows independent control over a variety of active and functional compounds without constraints placed on the others. Any plant matrix can work well in use in terms of enabling excellent homogeneity and distribution of ingredients. The method utilizes no solvents and thus requires no further processing or drying before packaging the product thereby offering great economic utility. The method creates free-flowing dry products that are directly amenable to packaging or rolling. The fully automated creation of pre-rolled herbal smoking products in a solventless fashion with tailored and homogeneous ingredients and flavors can be accomplished with the method at its core. In one refinement of the method, the particle size of the botanical substrate is tailored for the loading % and type of active molecules being adsorbed to the botanical substrate or coating layers thereof.

The method allows for the creation of multiple layers of ingredients. This may be used to operationally/functionally manufacture a product more easily than other methods efficiently and cost-effectively. The method of the system may offer novel product creations, such as where the last application is one where it is an antioxidant or another ingredient that may offer other stability or product lifetime protection purposes. Multiple steps could also be used to layer-on different ingredients which may not be initially compatible with each other and could not be introduced together all at once. This created compatibility may be beneficial to design onto the surface of the botanical substrate or its lamellar substrata, and this method would allow its manufacture.

The method can be conducted in autonomous and continuous fashions. The weighing of solids in metered amounts can be conducted in programmable, and repeatable, consistent amounts as is known to those skilled in the art. Liquid filling or injecting can be conducted in programmable, and repeatable, consistent amounts as is known to those skilled in the art. Transferring of containers into mixing units can be conducted in automated operations. Multiple autonomous operating conditions may be conducted sequentially use a programmable logic controller (PLC) and any useful programming language, to create a continuous operation of the method.

EXAMPLES

Example 1

An appropriate amount of marshmallow leaf is first collected and shaken on a 2 mm sieve. 44.27 grams of the leaf that has passed through the sieve is collected and placed in the container that will be inserted into the dual-asymmetric centrifuge. To this container is additionally added 4.23 grams of cannabigerol (CBG). The container is then placed in the mixer and the mixer is operated at 2000 RPM for 90 seconds. To the container is then added 1.5 grams of terpene formulation Tropical Trainwreck and the container is placed in the mixer which is then operated at 2000 RPM for 20 seconds. This example produces a product with 7.5% cannabigerol (CBG) and 3% Tropical Trainwreck terpenes on the botanical substrate.

Example 2

28.25 grams of the leaf that has passed through the sieve is collected and placed in the container and inserted into a dual-asymmetric centrifuge. To this container is additionally added 19.25 grams of CBG. The container is then placed in the mixer and the mixer is operated at 2000 RPM for 90 seconds. To the container is then added 2.0 grams of terpene formulation Tropical Trainwreck and the container is placed in the centrifuge which is then operated at 2000 RPM for 20 seconds. This example produces a product with 35% CBG and 4% Tropical Trainwreck terpenes on the botanical substrate.

Example 3

Cannabis concentrate in the form of Live Resin was gently warmed until fully melted, and placed in a freezer held between 0 degrees Celsius and 10 degrees Celsius overnight. The frozen concentrate is then ground using a mortar and pestle and the resulting powder is added to 7.5 grams of cannabis flower and leaf material that had previously been placed in the container. The container is then placed in the dual-asymmetric centrifuge (DAC) and the DAC is operated at 2000 RPM for 15 seconds. A visual inspection is performed and additional 15-second cycles in the DAC are performed until the mixture looks homogeneous. The cannabis concentrate is heated in the range from 25 degrees Celsius to 150 degrees Celsius. The cannabis concentrate is added at that elevated temperature or subsequently frozen to a temperature to solidify and process, which could be from −100 degrees Celsius to 24 degrees Celsius. In the example above the pre-cooling temperature was 6.3 degrees Celsius.

Example 4

To 7.5 grams of cannabis concentrate in the form of distillate was added 0.54 grams of terpene formulation Tsour Apricot and the mixture is warmed until free-flowing, approximately at 60 degrees Celsius. The resulting oil was then added to 14.25 grams of ground cannabis flower and leaf material that had been placed in the container and inserted into the dual-asymmetric centrifuge and the centrifuge is operated at 2000 RPM for 15 seconds. A visual inspection is performed and if necessary additional 15-second cycles in the centrifuge are performed until the mixture looks homogeneous. Distillate does not flow readily at room temperature with a viscosity at room-temperature typically in excess of 200,000 centipoise (cps). It needs to be heated to allow workable flowability. A range of good temperatures for this would be 30 degrees Celsius to 100 degrees Celsius. Cannabis can be ground in many ways, in this example, a hand grinder is used, but any herb grinder and a range of particle sizes may be used in the process. This example produced a 40% tetrahydrocannabinol (THC) product, as the distillate was 90% tetrahydrocannabinol (THC) and the botanical substrate cannabis was 15% tetrahydrocannabinol (THC). The final product had 2.5% Tsour Apricot terpenes.

Example 5

1.42 grams of cannabidiol (CBD) and 0.25 grams of flavor formulation (Tropical Trainwreck) were added to the container. The container was placed in the mixer and run for 2000 RPM for 30 seconds. The container was placed in a freezer for 4 hours. After this time 8.0 grams of ground hemp flower was added to the container and placed in the mixer which was subsequently operated at 2000 RPM for 30 seconds. This combines CBD isolate with a hemp botanical substrate that exhibits an initial CBD content of 13.8%. The CBD content is increased to a precise 25% overall when the process is completed. 2.5% terpenes are also added to the hemp material. This approach can be used to create a consistent, standardized, therapeutic/pharmaceutical cannabidiol (CBD) inhalable product.

The plurality of botanical substrates of desired particle size, preferably up to 20 mm and down to 0.1 mm are obtained by passing the botanical substrates through a sieve. Optionally, a 1 mm sieve is used for botanical substrates comprising marshmallow leaf. Material on both the top and the bottom of the sieve can be used. The container may be at room temperature, at colder temperatures, or even pre-heated before use. The container may be flushed/evacuated with nitrogen or argon, or other inert gas to produce an oxygen-free environment. The container may have modified lids, consisting of varying materials, which employ seals, valves, tubing connections, and the like, to enable efficient atmospheric evacuation and subsequent introduction of ingredients under inert atmospheres.

The mixer can be operated in a variety of mixing speeds encompassing such revolutions per minute (rpm) rates of as low as single digit rpms and going up to around 10,000 rpm. The duration of mixing can be from less than a second to many minutes.

The cannabinoid of interest for producing herbal smoking products that mimic the characteristics of cannabis or hemp could be in either an extract or isolated/pure form. Extracts can range in cannabinoid purity, from 10% up to 99% as some are oils themselves, and look like tetrahydrocannabinol (THC) distillate. The words distillate, extract, oil, isolate, and even compound/molecule in the context of describing a cannabinoid-rich material may be used to describe the types of inputs that could be used in the process. Cannabis sativa includes both marijuana and hemp. Hemp generally comprises less than 0.3% by weight tetrahydrocannabinol (THC) and tetrahydrocannabinolic acid (THCA), and marijuana generally comprises greater than 0.3% by weight tetrahydrocannabinol (THC) and tetrahydrocannabinolic acid (THCA) in the flowering tops of the plant. In some examples herein, the composition comprises *Cannabis sativa* in the form of hemp and does not comprise marijuana. In some examples, the composition comprises *Cannabis sativa* in the form of marijuana and does not comprise hemp. In some examples, the composition comprises *Cannabis sativa* in the form of both marijuana and hemp.

TABLE 1

Marijuana Active and Inactive Placebo Compositions using Non-Cannabis Botanical Base.

| Formulation Name | Total THC (% by mass) | Total CBD (% by mass) | Total Terpenes (% by mass) | Botanical Base (% by mass) |
|---|---|---|---|---|
| Standard THC Cannabis | 10.0% | 2.0% | 2.0% | 86.0% |
| 75% THC Placebo | 7.5% | 2.0% | 2.0% | 88.5% |
| 50% THC Placebo | 5.0% | 2.0% | 2.0% | 91.0% |
| 25% THC Placebo | 2.5% | 2.0% | 2.0% | 93.5% |
| 0% THC Placebo | 0.0% | 2.0% | 2.0% | 96.0% |
| 1:1 THC:CBD | 5.0% | 5.0% | 2.0% | 88.0% |
| 1:20 THC:CBD | 0.5% | 10.0% | 2.0% | 87.5% |
| 0% Cannabinoids | 0.0% | 0.0% | 2.0% | 98.0% |
| 0% Cannabinoids + 500% Terpenes | 0.0% | 0.0% | 10.0% | 90.0% |

TABLE 2

Tobacco Active and Inactive Placebo Compositions using Non-Tobacco Botanical Base.

| Formulation Name | Total Nicotine (% by mass) | Total Aromatics (% by mass) | Botanical Base (% by mass) |
|---|---|---|---|
| Dried Tobacco | 1.3% | 1.0% | 97.8% |
| 75% Nicotine | 0.9% | 1.0% | 98.1% |
| 50% Nicotine | 0.6% | 1.0% | 98.4% |
| 25% Nicotine | 0.3% | 1.0% | 98.7% |
| 0% Nicotine Placebo | 0.0% | 1.0% | 99.0% |
| 1:1 Nicotine:Aromatics | 1.0% | 1.0% | 98.0% |
| 1:20 Nicotine:Aromatics | 0.1% | 2.0% | 97.9% |
| 0% Nicotine + 500% Aromatics | 0.0% | 5.0% | 95.0% |

It should be understood that the embodiments of the system disclosed herein are illustrative of the principles of the system. Other modifications that may be employed are within the scope of the system. Thus, by way of example, but not of limitation, alternative configurations of the system may be utilized in accordance with the teachings herein. Accordingly, the system is not limited to that precisely as shown and described.

What is claimed is:

1. A method of producing coated botanical substrates i, wherein the method comprises the steps of: (i) adding an active ingredient into a container containing a botanical substrate, wherein the active ingredient is a cannabinoid or nicotine; (ii) mixing said container containing a botanical substrate and the active ingredient without the use of solvents until the active ingredient is adsorbed to the surface of the botanical substrate to produce a coated botanical substrate having a primary coating of the active ingredient on the substrate.

2. The method of claim 1, wherein the cannabinoid comprises at least one of Δ-9-tetrahydrocannabinol (D9-THC) cannabidiol (CBD), cannabigerolic acid (CBGA), cannabigerol (CBG), cannabigerol monomethylether (CBGM), cannabigerovarin (CBGV), cannabichromene (CBC), cannabichromevarin (CB CV), cannabidiol monomethylether (CBDM), cannabidiol-C4 (CBD-C4), cannabidivarin (CBDV), cannabidiorcol (CBD-C1), Δ-9-tetrahydrocannabinolic acid A (THCA-A), Δ-9-tetrahydrocannabionolic acid B (THCA-B), Δ-9-tetrahydrocannabinolic acid-C4 (THCA-C4), Δ-9-tetrahydrocannabinol-C4, Δ-9-tetrahydrocannabivarin (THCV), Δ-9-tetrahydrocannabiorcol (THC-C1), Δ-7-cis-iso tetrahydrocannabivarin, Δ-8-tetrahydrocannabinol (D8-THC), cannabicyclol (CBL), cannabicyclovarin (CBLV), cannabielsoin (CBE), cannabinol (CBN), cannabinol methylether (CBNM), cannabinol-C4 (CBN-C4), cannabivarin (CBV), cannabinol-C2 (CBN-C2), cannabiorcol (CBN-C1), cannabinodiol (CBND), cannabinodivarin (CBVD), cannabitriol (CBT), 10-ethoxy-9hydroxy-A-6a-tetrahydrocannabinol, 8,9-dihydroxy-Δ-6a- tetrahydrocannabinol, cannabitriolvarin (CBTV), ethoxy-cannabitriolvarin (CB TVE), dehydrocannabifuran (DCBF), cannabifuran (CBF), cannabichromanon (CBCN), cannabicitran (CBT), 10-oxo-A-6a-tetrahydrocannabionol (OTHC), Δ-9-cis-tetrahydrocannabinol (cis-THC), 3,4,5,6-tetrahydro-7-hydroxy-α-α-2-trimethyl-9-n-propyl-2, 6-methano-2H-1- benzoxocin-5-methanol (OH-iso-HHCV), cannabiripsol (CBR), trihydroxy-Δ-9- tetrahydrocannabinol (triOH-THC), cannabinol propyl variant (CBNV), cannabidiolic acid (CBDA), cannabitriol (CBO), and tetrahydrocannabivarinic acid (THCVA) and all isomers and analogues of the above.

3. The method of claim 2, wherein the cannabinoid is obtained as an extract or purified form comprising liquids, solids, semi-solids, slurries, botanical substrate pastes, and wetted solids.

4. The method of claim 2, wherein the coated botanical substrate has a coated particle mass (grams), wherein the botanical substrate has a mass that ranges from 55% to 99.3% of the coated particle mass, the cannabinoid in the coated botanical substrate has a mass that ranges from 0.5% to 35% of the coated particle mass, and the flavoring agent in the coated botanical substrate has a mass that ranges from 0.2% to 10% of the coated particle mass.

5. The method of claim 1, wherein the botanical substrate comprises a plurality of botanical substrates.

6. The method of claim 1, wherein the active ingredient is not diluted with solvents or other solutions that are intended to be removed from a final product.

7. The method of claim 1, wherein the active ingredient is nicotine.

8. The method of claim 7, wherein the botanical substrate is coated with nicotine and with at least one terpene to produce a tobacco tapering product.

9. The method of claim 7, wherein the botanical substrate is coated with nicotine and without terpenes to produce a tobacco tapering product.

10. The method of claim 1, wherein a flavoring agent is added into the container comprising the botanical substrate coated with the active ingredient and the container is added to a mixer and the mixer is activated until the flavoring agent is substantially adsorbed.

11. The method of claim 10, wherein the method comprises centrifuging the container from 20 to 10,000 RPM for about 0.9 to 90 seconds to substantially adsorb the flavoring agent onto the surface of the botanical substrate and adsorbed active ingredient.

12. The method of claim 10, wherein the flavoring agent comprises a terpene profile of a *cannabis* plant.

13. The method of claim 1, wherein the method optionally comprises one or more of: (a) pre-cooling the container before mixing, (b), pre-heating the container before mixing and (c) evacuating the container to then fill with an inert gas to produce an oxygen-poor environment.

14. The method of claim 13, wherein the pre-cooling of the container is performed at about 20 degrees C., 10 degrees C., 5 degrees C., 0 degrees C., −5 degrees C., −10 degrees C., −15 degrees C., −20 degrees C., −25 degrees C., −30 degrees C., −40 degrees C., −78 degrees C. or at or below −79 degrees C.

15. The method of claim 1, wherein the method comprises centrifuging the container from 20 to 10,000 RPM for about 0.9 to 90 seconds to produce the primary coating of the active ingredient on the botanical substrate.

16. The method of claim 1, wherein the botanical substrate has an average particle size ranging from 0.1 mm to 20 mm.

17. The method of claim 1, wherein the botanical substrate comprises *Althaea officinalis, Amaranthus dubius, Arctostaphylos uva-ursi, Argemone mexicana, Arnica* spp., *Artemisia vulgaris, Brassica oleracea, Calea zacatechichi, Cannabis sativa, Canavalia maritima, Cecropia obtusifolia, Cestrum nocturnum, Cynoglossum virginianum, Cytisus scoparius, Entada rheedii, Eschscholzia* ca/fomica, *Fittonia albivenis, Humulus lupulus, Lavandula* spp, *Lactuca virosa, Lamiaceae* spp., *Salvia* spp, *Scutellaria* spp, *Leonotis leonurus, Leonurus cardiaca, Leonurus sibiricus, Lobelia cardinalis, Lobelia inflata, Lobelia siphilitica, Matricaria chamomilla, Nepeta cataria, Nicotiana, Nymphaea alba, Nymphaea caerulea, Papaver somniferum, Origanum majorana, Origanum vulgare, Passiflora incarnata, Pedicularis densiflora, Pedicularis groenlandica, Rubus idaeus, Rubus occidentalis, Salvia divinorum, Salvia dorrii, Scutellaria galericulata, Scutellaria lateriflora, Scutellaria nana, Sida acuta, Sida rhombifolia, Silene capensis, Syzygium aromaticum, Tagetes lucida, Tarchonanthus camphoratus, Turnera diffusa, Tussilago farfara, Verbascum* spp, *Zornia latifolia*, or mixtures thereof.

18. The method of claim 1, wherein the mixing is done in a mixer and wherein the mixer is a dual asymmetrical centrifuge (DAC) mixer.

19. The method of claim 18, wherein the active ingredient is nicotine, wherein the coated botanical substrate comprises a plurality of coated botanical substrates having a coated particle mass (grams), wherein the plurality of botanical substrates has a mass that ranges from 95% to 99% of the coated particle mass, the nicotine in the plurality of coated botanical substrates has a mass that ranges from 0.1% to 1.3% of the total coated particle mass, and the flavoring agent in the plurality of coated botanical substrates has a mass that ranges from 1% to 5% of the total coated particle mass.

20. The method of claim 1, wherein the method further comprises coating the botanical substrate with additional ingredients that help to stabilize a herbal smoking product formed with the coated botanical substrate.

21. The method of claim 1, wherein the cannabinoid is without terpenes to produce a *cannabis* placebo product.

22. The method of claim 1, wherein the cannabinoid has at least one terpene to produce a *cannabis* placebo product.

* * * * *